United States Patent
Cobley et al.

(10) Patent No.: US 6,528,687 B2
(45) Date of Patent: Mar. 4, 2003

(54) RUTHENIUM COMPLEXES AND THEIR USE IN ASYMMETRIC HYDROGENATION

(75) Inventors: Christopher James Cobley, Cambridge (GB); Julian Paul Henschke, Cambridge (GB); James Andrew Ramsden, Cambridge (GB)

(73) Assignee: Chirotech Technology Limited, Cambridge (GB)

( * ) Notice: Subject to any disclaimer, the term of this patent is extended or adjusted under 35 U.S.C. 154(b) by 0 days.

(21) Appl. No.: 09/911,059

(22) Filed: Jul. 23, 2001

(65) Prior Publication Data

US 2002/0095056 A1 Jul. 18, 2002

(30) Foreign Application Priority Data

| Jul. 24, 2000 | (GB) | 0018146 |
| Aug. 4, 2000 | (GB) | 0019227 |
| Jan. 19, 2001 | (GB) | 0101458 |
| Mar. 8, 2001 | (GB) | 0105742 |

(51) Int. Cl.$^7$ .......................................... C07C 209/52
(52) U.S. Cl. .................... 564/415; 564/413; 564/448; 564/487; 564/489
(58) Field of Search ................ 564/413, 415, 564/448, 487, 489

(56) References Cited

U.S. PATENT DOCUMENTS 5,504,253 A * 4/1996 Van Wagenen et al. ...... 564/374
5,686,616 A * 11/1997 Tani et al. ................... 546/185

FOREIGN PATENT DOCUMENTS

| EP | 0 718 265 A2 | 6/1996 |
| EP | 0 916 637 A1 | 5/1999 |

OTHER PUBLICATIONS

Abdur–Rashid et al, 'RuH(diphosphine)(diamine): catalyst precursors for the stereoselective hydrogenation of ketones and imines.' Organometallics 2001, 20, pp. 1047–1049.*
Abdur–Rashid, K. et al., "Synthesis of Chiral alcohols and Amines by RuH$_2$(diphospine)(diamine) Catalysed Hydrogenation of Ketones and Imines," University of Toronto, Dept. of Chemistry, CSC2000 Program (2000), http://www.chem.ucalgary.ca/csc2000/program/00000344.htm.
Abdur–Rashid, K. et al., "RuHCl(diphosphine)(diamine): Catalyst Precursors for the Stereoselective Hydrogenation of Ketones and Imines," Organometallics, (Feb. 21, 2001) 20:1047–1049; presented at the Canadian Society for Chemistry Conference, Calgary, May 2000.
Akotsi, O. M., et al., "Versatile Precursor to Ruthenium–Bis(phoshine) Hydrogenation Catalysts," Chirality (2000) 12:514–522, Wiley–Liss, Inc.

Bianchini, C., et al., "Enantioselective Hydrogenation of 2–Methylquinoxaline to (–)–(2S)–2–Methyl–1,2,3,4–tetrahydroquinoxaline by Irudium Catalysis," Organometallics (Jun. 1998) 17:3308–3310, American Chemical Society.
Blaser, H., et al., "Enantioselective Catalysis for Agrochemicals. The Case Histories of (S)–metolachlor, (R)–metalaxyl and clozylacon," Topics in Catalysis (1997) 4:275–282, J.C. Baltzer AG, Science Publishers.
Cao, P., et al., "Ru–BICP–Catalyzed Asymmetric Hydrogenation of Aromatic Ketones," J. Org. Chem. (Feb. 1999) 64:2127–2129 [XP–002169915], American Chemical Society.
Chan, Y.N.C., et al., "Chemoselective Hydrogenation of Imines Catalysed by Ir$^{III}$ Complexes," J. Chem. Soc., Chem. Commun. (1990) 869–871.
Chan, Y.N.C., et al., "Iridium (III) Hydride Complexes for the Catalytic Enantioselective Hydrogenation of Imines," J. Am. Chem. Soc. (1990) 112:9400–9401, American Chemical Society.
Doucet, H., et al., "trans–[RuCl$_2$(phosphane)$_2$(1,2–diamine)] and Chiral trans–[RuCl$_2$(diphosphane)(1,2–diamine): Shelf–Stable Precatalysts for the Rapid, Productive, and Steroselective Hydrogenation of Ketones," Angew. Chem. Int. Ed. (1998) 37(12):1703–07; Wiley–VCH Verlag GmbH (German version: Angew. Chem. 1998, 110:1792–96.
Kobayashi, S., et al., "Catalytic Enantioselective Addition to Imines," Chem. Rev. (Apr. 1999) 99:1069–1094, American Chemical Society.
Ohkuma, T., et al., "Asymmetric Hydrogenation of Alkenyl, Cyclopropyl, and Aryl Ketones. RuCl$_2$(xylbinap)(1,2–diamine) as a Precatalyst Exhibiting a Wide Scope," J. Am. Chem. Soc. (Dec. 1998) 120:13529–13530, American Chemical Society.

(List continued on next page.)

Primary Examiner—Brian J. Davis

(57) ABSTRACT

A process for the preparation of an enantiomerically enriched chiral amine of formula (10), or the opposite enantiomer thereof, from an inline of formula (11)

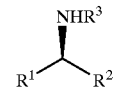

(10)

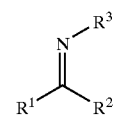

(11)

wherein (i) $R^1$ is aryl, $R^2$ is alkyl and $R^3$ is aryl or aryl-$CH_2$—, or (iii) $R^2$ is linked with $R^1$ and/or $R^3$ to form one or more rings and $R^3$ or $R^1$ (if not in a ring) is H or a non-interfering organic group, the number of C atoms in each of $R^1$, $R^2$ and $R^3$ being up to 30, comprises asymmetric hydrogenation of the imine in the presence of a base and, as catalyst, a ruthenium complex of a chiral diphosphine and a chiral diamine.

28 Claims, No Drawings

OTHER PUBLICATIONS

Ohkuma, T., et al., "Practical Enantioselective Hydrogenation of Aromatic Ketones," *J. Am. Chem. Soc.* (1995) 117(9):2675–76, American Chemical Society.

Ohkuma, T., et al., "Preferential Hydrogenation of Aldehydes and Ketones," *J. Am. Chem. Soc.* (1995) 117(41):10417–10418, American Chemical Society.

Sablong, R., et al., "Asymmetric Hydrogenation of Imines Catalysed Carboxlato(diphosphine)iridiuym (III) Complexes", *Tetrahedron: Asymmetry* (1996) 7(11):3059–62, Elsevier Science Ltd. in Great Britain.

Sablong, R., et al., "The Asymmetric Hydrogenation of Imines Using Tridentate $C_2$ Diphosphine Complexes of Iridium(I) and Rhodium(I)", *Tetrahedron Letters* (1996) 37(28):4937–40, Elsevier Science Ltd. in Great Britain.

Schnider, P., et al., "Enantioselective Hydrogenation of Imines with Chiral (Phosphanodihydrooxazole)iridium Catalysts," *Chem. Eur. J.* (1997) 3(6):887–892, VCH Verlagsgesellschaft mbH.

Spindler, F., et al., "Novel Diphosphinoiridium Catalysts for the Enantioselective Hydrogenation of N–Arylketimines," *Angew. Chem. Int. Ed. Engl.* (1990) 29(5):558–9, VCH Verlagsgesellschaft mbH.

Willoughby, C.A., et al., "Asymmetric Titanocene–Cataylzed Hydrogenation of Imines", *J. Am. Chem. Soc.* (1992) 114(19):7562–64, American Chemical Society.

Willoughby, C.A., et al., "Catalytic Asymmetric Hydrogenation of Imines with a Chiral Titanocene Catalyst: Kinetic and Mechanistic Investigations", *J. Am. Chem. Soc.* (1994) 116(26):11703–14, American Chemical Society.

Willoughby, C.A., et al., "Catalytic Asymmetric Hydrogenation of Imines with a Chiral Titanocene Catalyst: Scope and Limitations", *J. Am. Chem. Soc.* (1994) 116(20): 8952–65, American Chemical Society.

\* cited by examiner

RUTHENIUM COMPLEXES AND THEIR USE IN ASYMMETRIC HYDROGENATION

FIELD OF THE INVENTION

This invention relates to ruthenium complexes bearing a chiral diphosphine and a chiral diamine and their use as catalysts for the asymmetric hydrogenation of imines.

In this context and throughout the following text, the term "catalyst(s)" refers to the isolated pre-catalyst that is added to the reaction vessel for hydrogenation and which typically undergoes a change in composition in situ to generate one or more catalytically active species.

BACKGROUND OF THE INVENTION

Although many highly enantioselective chiral catalysts are available for the asymmetric hydrogenation of C=C and C=O bonds, relatively few exist for effective reduction of the analogous C=N function. The production of chiral amines via this methodology still represents a major challenge. In the past ten years, progress in this field has been made with catalysts based on complexes of rhodium, iridium, ruthenium and titanium, with most recent emphasis being devoted to Ir and Ti.

A recent review provides a comprehensive summary of the most important advances in this field (Kobayashi and Ishitani, *Chem. Rev.*, 1999, 99, 1069); representative examples include those detailed below. Osborn and co-workers developed chiral Ir complexes of the type [Ir(P—P)HI$_2$]$_2$ (1), in which (P—P) represents a chiral ligand, and analogues thereof, see Chan and Osborn, *J Am. Chem. Soc.*, 1990, 112, 9400; Chan et al., *J Chem. Soc., Chem. Commun.*, 1990, 869; Sablong and Osborn, *Tetrahedron Lett.*, 1996, 37, 4937. Although these systems showed reasonable activities, the enantioselectivites were in general only moderate, despite employing various chiral diphosphines (e.g. up to 35% ee for the cyclic imine 2). Spindler et al. independently reported an in situ prepared Ir catalyst incorporating JOSIPHOS (3) as the chiral ligand, and subsequently applied it to the industrial production of (S)-Metolachlor (4) (Spindler et al., *Angew. Chem., Int. Ed Engl.*, 1990, 29, 558; Blaser and Spindler, *Topics in Catalysis*, 1997, 4, 275).

Buchwald and co-workers have prepared chiral titanocene complexes 5 and 6, and have effectively employed them in reductive amination of a range of imines (Willoughby and Buchwald, *J Am. Chem. Soc.*, 1992, 114, 7562; *J Am. Chem. Soc.*, 1994, 116, 8952; *J Am. Chem. Soc.*, 1994, 116, 11703). These catalysts are effective in both asymmetric hydrogenation and asymmetric hydrosilylation processes, although their practical utility is limited by (a) the requirement for high operating pressures (typically >60 bar H$_2$) in the former and (b) the requirement to activate the catalyst in the reaction vessel by addition of butyl-lithium and phenyl silane. More recently, Pfaltz and co-workers have employed an Ir phosphine-oxazolidine complex (7) for the asymmetric hydrogenation of various prochiral imines. Although N-(phenylethylidene)aniline was successfully reduced in 99% yield with 89% ee, the use of cyclic imines as substrates resulted in much lower enantioselectivities (Schnider et al, *Chem. Eur. J.*, 1997, 3, 887). Lastly, Bianchini et al. have addressed the asymmetric hydrogenation of 2-methylquinoxaline (8), which is challenging due to the aromatic nature of the substrate (Bianchini et al., *Organometallics*, 1998, 17, 3308). Ee's of up to 90% (at 54% substrate conversion) were achieved using the ortho-metalated dihydride complex (9) as catalyst, although at 96.5% substrate conversion the ee decreased to 73%.

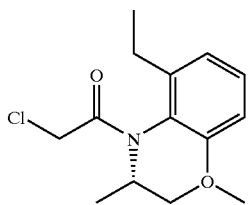

(4)

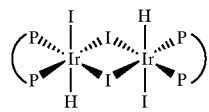

(1)

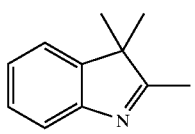

(2)

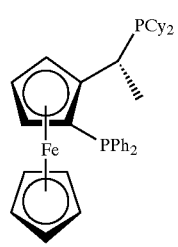

(3)

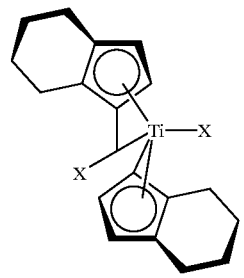

(5)

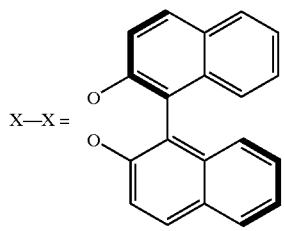

(6)

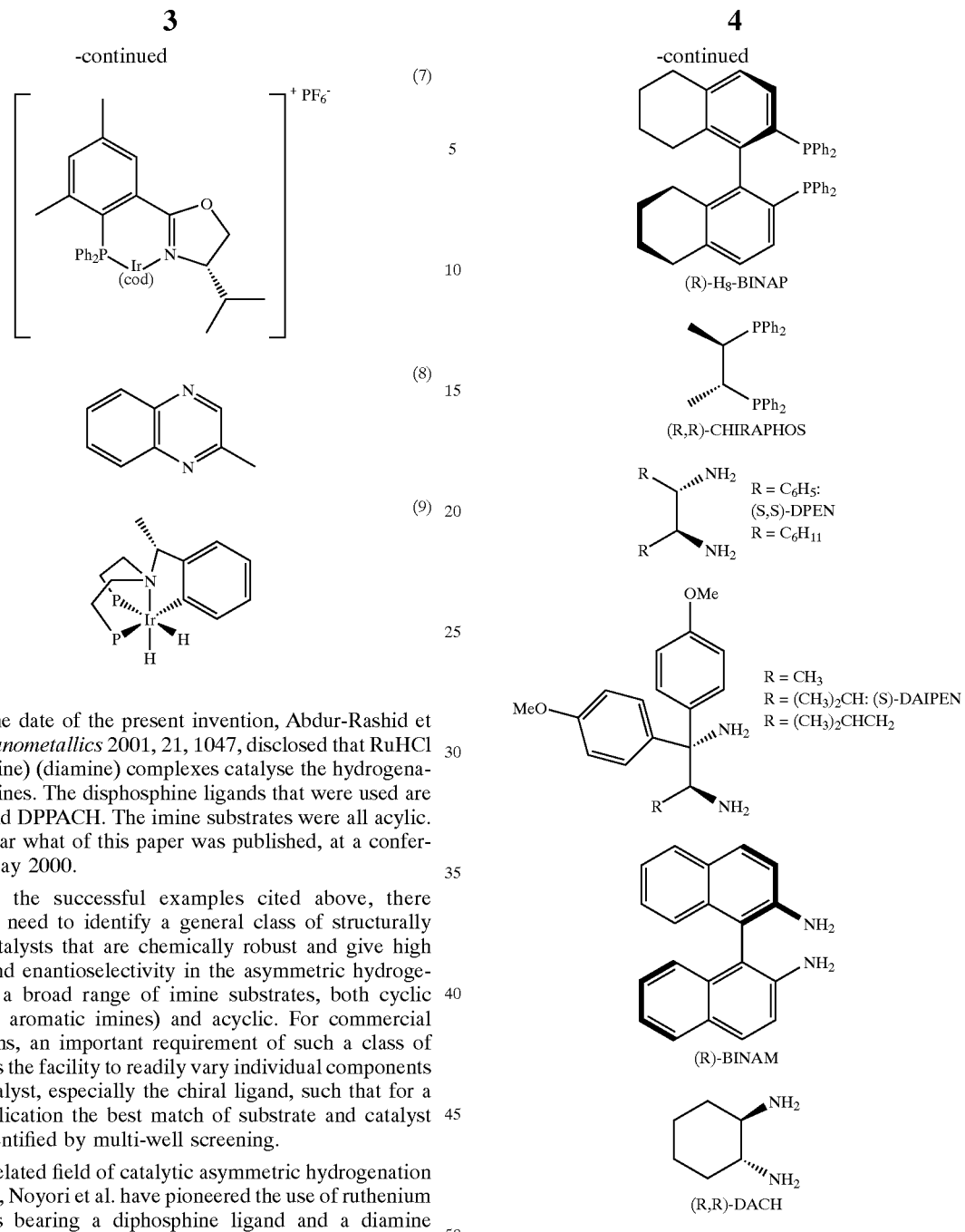

After the date of the present invention, Abdur-Rashid et al, in *Organometallics* 2001, 21, 1047, disclosed that RuHCl(diphosphine)(diamine) complexes catalyse the hydrogenation of imines. The disphosphine ligands that were used are BINAP and DPPACH. The imine substrates were all acylic. It is unclear what of this paper was published, at a conference in May 2000.

Despite the successful examples cited above, there remains a need to identify a general class of structurally related catalysts that are chemically robust and give high activity and enantioselectivity in the asymmetric hydrogenation of a broad range of imine substrates, both cyclic (including aromatic imines) and acyclic. For commercial applications, an important requirement of such a class of catalysts is the facility to readily vary individual components of the catalyst, especially the chiral ligand, such that for a given application the best match of substrate and catalyst can be identified by multi-well screening.

In the related field of catalytic asymmetric hydrogenation of ketones, Noyori et al. have pioneered the use of ruthenium complexes bearing a diphosphine ligand and a diamine ligand. At least one and usually both of these ligands are chiral. Initial studies of these complexes, as reported in EP-A-0718265, demonstrated the highly efficient reduction of unfunctionalised aromatic ketones. Examples of chiral diphosphines employed were BINAP, Tol-BINAP, Xylyl-BINAP, H₈BINAP and CHIRAPHOS. Examples of chiral diamines employed were DPEN, DAIPEN and others.

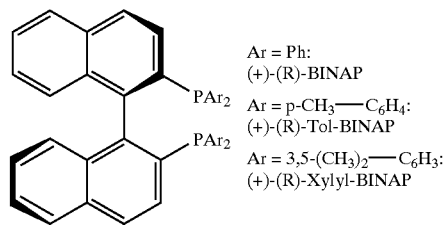

It was subsequently disclosed by R. Noyori and co-workers (Ohkuma et al., *J. Am. Chem. Soc.*, 1995, 107,2675 and 10417) that a fully characterised diphosphine-ruthenium-diamine complex could be isolated and used as the catalyst. In particular, high productivity and high selectivity were always associated with the use of the chiral biaryl-phosphines Tol-BINAP and Xylyl-BINAP and the chiral diamines DPEN and DAIPEN (Doucet et al., *Angew. Chem. Int. Ed.* 1998, 37, 1703 and Ohkuma et al., *J Am. Chem. Soc.*, 1998, 120, 13529). Analogous catalysts incorporating the DuPHOS family of ligands have recently been prepared (Akotsi et al., *Chirality*, 2000, 12, 514), although their application to the asymmetric hydrogenation of ketones or imines has not been reported.

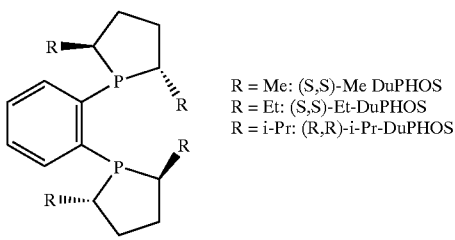

R = Me: (S,S)-Me DuPHOS
R = Et: (S,S)-Et-DuPHOS
R = i-Pr: (R,R)-i-Pr-DuPHOS

SUMMARY OF THE INVENTION

According to the present invention, a ruthenium complex, bearing a chiral diphosphine and chiral diamine, is used in the asymmetric hydrogenation of a diverse range of prochiral imines. When in the presence of a base, such catalysts can be used to produce chiral amines with high to excellent enantioselectivites, in some cases better than those methods reported to date.

The present invention provides an effective means of accessing an enantiomerically enriched chiral amine of formula (10), or the opposite enantiomer thereof, from an imine of formula (11), according to the following reaction:

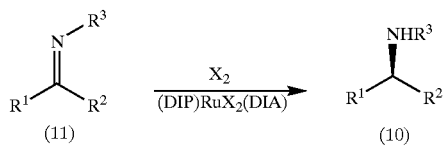

wherein the catalyst is shown for the purpose of illustration, (i) $R^1$ is aryl, $R^2$ is alkyl and $R^3$ is aryl or aryl-$CH_2$—, or (ii) $R^2$ is linked with $R^1$ and/or $R^3$ to form one or more rings and $R^3$ or $R^1$ (if not in a ring) is H or a non-interfering organic group, the number of C atoms in each of $R^1$, $R^2$ and $R^3$ being up to 30. The novel process comprises asymmetric hydrogenation of the imine in the presence of a base and, as catalyst, a ruthenium complex of a chiral diphosphine and a chiral diamine.

DESCRIPTION OF THE INVENTION

In the illustrative reaction shown above, $(DIP)RuX_2(DIA)$ represents the ruthenium complex that, following activation with base, catalyses the asymmetric hydrogenation process. DIP is a bis-tertiary phosphine in which the two phosphorus atoms are linked by a $C_{2-7}$ carbon chain such that they form a 5–10 membered ring with the Ru atom, DIA is a diamine (typically vicinal) with any aromatic, alkyl or hydrogen substituent on the $C_2$— carbon chain linking the nitrogen atoms, and X is halide or carboxylate, preferably halide (Cl, Br, I or F) and more preferably chloride. Both DIP and DIA are chiral and substantially in the form of a single enantiomer.

In preferred embodiments of the present invention, DIP in the complex $(DIP)RuX_2(DIA)$ is selected from one of two sub-classes of bis-tertiary phosphine. Firstly, an atropisomeric bis-tertiary phosphine may be used, in which the two phosphorus atoms are linked by a biaryl backbone. Representative members of this subclass include the BINAP ligands depicted above, and ligands based on a biphenyl backbone, such as the BIPHEP/BIPHEMP (respectively Y=OMe/Y=Me) series of formula (12), in which Ar is a phenyl group optionally substituted with up to two alkyl groups and $(X)_n$ represents one or more non-interfering substitutents. The second subclass of ligands are those in which each phosphorus atom forms part of a four-membered (phosphetane) or five-membered (phospholane) ring. The DuPHOS series of ligands are representative of this subclass; in formula (13), R is $C_{1-6}$ linear or branched alkyl and is preferably methyl or ethyl.

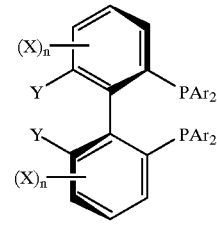

(12)

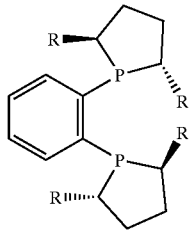

(13)

It will be understood by those of ordinary skill in the art that a formula such as (13) represents the active nucleus of DuPHOS ligands and that it may be substituted without affecting its function. Minor modifications may also be made to other ligands described herein, to give functionally equivalent entities.

One class of imines that can be hydrogenated according to this invention is acyclic, wherein $R^1$ is aryl, $R^2$ is alkyl and $R^3$ is aryl or aryl-$CH_2$—. For example, each aryl group (which, for the purposes of this specification, includes heteroaryl) is phenyl optionally substituted by one or more substituents having up to 6 C atoms, and $R^2$ is methyl or another alkyl group of up to 6 C atoms. Representative acyclic substrates of this type are N-(1-phenylethylidene) aniline and N-(1-phenylethylidene)benzylamine.

Another class of acyclic imines comprises those where $R^1$ and $R^2$ are linked to form a ring; these substrates are acyclic because the C=N bond is not in a ring. A representative example is N-(2,3-dihydro-1H-indan-2-ylidene) benzylamine.

Yet another class of imine substrates is cyclic, wherein $R^2$ and $R^3$ are linked to form a ring, e.g. a cycloalkyl or heterocyclic ring (typically of 5 or 6 atoms) which may have a fused benzene or other aromatic ring, or wherein $R^1$, $R^2$ and $R^3$ are linked. Any group which is not in the cyclic imine ring, i.e. $R^1$, may be H or, for example, an alkyl or other group having up to 6 C atoms, but may be a bulkier hydrocarbon or other group provided that, as can readily be determined by one of ordinary skill in the art, it does not interfere in the hydrogenation reaction.

Representative cyclic substrates are dihydroquinolines and dihydroisoquinolines. The preferred ligand in the latter case at least is of the DuPHOS type.

Other representative cyclic substrates are indolenines, isoquinolines and quinoxalines. One preferred ligand type in such a case is biaryl, e.g. of the HexaPHEMP type (PCT/GB01/02467). These are of formula (12) wherein Y is $CH_3$, n is 2 and each X is $CH_3$, i.e. [4,4',5,5',6,6'-hexamethyl(1, 1'-diphenyl)-2,2'-diyl]bis(diarylphosphine) ligands.

It will be appreciated that certain ligands may be preferred in conjunction with certain substrates. Thus, it is apparent from Examples 4–6 that the biaryl class of ligands may be better suited to cyclic imines whereas DuPHOS ligands work better with acyclic imines. In some cases, particular combinations give especially good results. However, a practitioner skilled in the art would recognise that any deviation from any trend would be evident on a case-by-case basis through a screening protocol, in which numerous combinations of ligand (DIP) and diamine (DIA) would be examined.

Also in preferred embodiments of the present invention, DIA in the complex (DIP)RuX$_2$(DIA) is a diamine of formula (14), in which at least one of the amine-bearing centres is stereogenic, $R_1$, $R_2$, $R_3$ and $R_4$ are independently H, $C_{1-20}$ alkyl or $C_{6-20}$ aromatic, and any pair of $R_1$, $R_2$, $R_3$ and $R_4$ is optionally linked to form one or more rings.

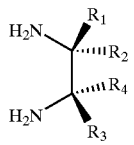

(14)

Compounds 15–19 and the opposite enantiomers are representative diamines. Another feature of the present invention is that, in certain cases, optimum performance of the catalyst is reliant on a given enantiomer of the DIP ligand being combined with the correct enantiomer of diamine. This matched-pair effect is evident for the use of DuPHOS ligands in Example 4 (compare entries 5 and 7 in the table following Example 4). Accordingly, the diamine (R,R)-DPEN is preferably combined with either (R,R)-methyl DuPHOS or (R,R)-ethyl DuPHOS, and the matching of (S,S)-stereoisomers is likewise effective.

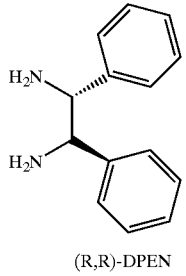

(R,R)-DPEN (15)

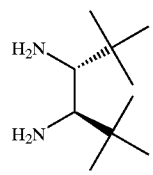

(16)

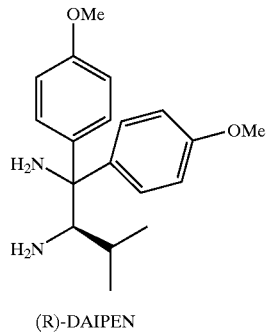

(R)-DAIPEN (17)

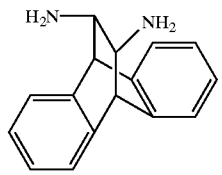

(R,R)-ANDEN (18)

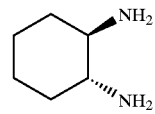

(R,R)-DACH (19)

Successful operation of the process of the present invention requires the presence of a base, preferably an alkali metal alkoxide, for example potassium t-butoxide or sodium diisoproproxide, which is easily separated from the product by standard extractive work-up procedures. Most preferably, the base is potassium t-butoxide. The amount of base relative to the imine substrate is in the range of 0.01–2.0 molar equivalents and more usually is typically in the range of 0.05–1.0 molar equivalents. For certain imine substrates, especially those prone to isomerisation with respect to position of the C=N bond, it is advantageous to reduce the amount of base to around 0.05 equivalents or lower, in order to achieve acceptable enantioselectivity. This effect is evident from Example 7 (below), for the ketimine (20). Control experiments, in the absence of catalyst, show facile equilibration of (20) to racemic aldimine (21) in the presence of 1.0 equivalent of potassium t-butoxide. Aldimine (21) is also a hydrogenation substrate but such hydrogenation does not generate a chiral centre.

(20;E:Z = 11.4:1.0)    (21)

For operation of the present invention, other characteristic features of preferred embodiments are as follows:

i) the reaction solvent is selected from isopropanol, ethanol, toluene, benzene, chlorobenzene and tetrahydrofuran; optionally, for liquid substrates (or solid substrates that melt below the reaction temperature), the solvent can be omitted.

ii) when a solvent is used, the substrate concentration is at least 0.5 M and more preferably is at least 3 M, since raising the concentration can improve the rate of reaction and/or the extent of substrate conversion.

iii) the reaction temperature is in the range 10–100° C. and, in order to achieve good substrate conversion, is normally at least 40° C.

iv) the reaction pressure is in the range 1–100 bar and, in order to achieve good substrate conversion, is normally at least 5 bar.

In summary, the process of the present invention provides an effective means of preparing a wide range of enantiomerically enriched chiral amines. In order to be economically viable, it is important that enantiomeric enrichment of the amine (10) is at least 50% ee, and is preferably at least 80% ee, or higher. If necessary, any shortfall in ee can subsequently be corrected by formation and crystallisation of a suitable acid salt form of the amine with a chiral acid or with an achiral acid conferring a conglomerate properties or a favourable eutectic composition. For commercial operation of the process, it is also important to effect good conversion of substrate to product, of at least 80% conversion and preferably at least 90% conversion.

The invention is further illustrated by the following Examples. Examples 1–3 relate to the synthesis of complexes, while Examples 4–8 relate to hydrogenation. More particularly, the substrates used in Examples 4 and 7 are acyclic imines, while those used in Examples 5, 6 and 8 are cyclic.

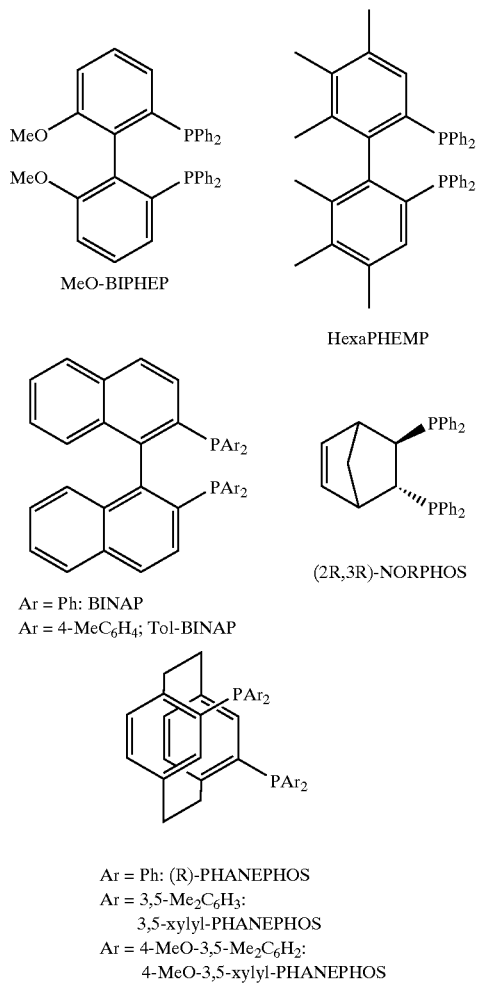

Example 1

[(R,R)-Me-DuPHOS-RuCl$_2$-(R,R)-DPEN]

[Ru(C$_6$H$_6$)Cl$_2$]$_2$ (150 mg, 0.30 mmol) and (R,R)-Me-DuPHOS (184 mg, 0.60 mmol) were placed in a Schlenk tube which was degassed and filled with nitrogen three times. Anhydrous, degassed DMF (3 mL) was then added and the reaction was heated at 100° C. for 60 minutes to give a deep red/brown solution. The solvent was removed under vacuum. (S,S)-DPEN (127 mg, 0.60 mmol) was then added and the tube evacuated and filled with nitrogen a further three times. Anhydrous, degassed CH$_2$Cl$_2$ (4 mL) was added and the reaction mixture was stirred for a further 60 minutes at room temperature. After removal of all volatiles in vacuo, the residue was suspended in Et$_2$O (5 mL), filtered, and the filtrate evaporated to dryness to yield a tan-coloured solid. $^{31}$P NMR: 93.4 ppm (s). This tan solid residue is a suitable catalyst for the hydrogenation of imines.

Example 2

[(R,R)-Et-DuPHOS-RuCl$_2$-(R,R)-DPEN]

[(R,R)-Et-DuPHOS-RuCl$_2$-(R,R)-DPEN] was prepared as described above for [(R,R)-Me-DuPHOS-RuCl$_2$-(R,R)-DPEN] using (R,R)-Et-DuPHOS. $^{31}$PNMR: 91.1 ppm (s).

Example 3

[(R,R)-i-Pr-DuPHOS-RuCl$_2$-(S,S)-DPEN]

[(R,R)-i-Pr-DuPHOS-RuCl$_2$-(S,S)-DPEN] was prepared as described above for [(R,R)-Me-DuPHOS-RuCl$_2$-(R,R)-DPEN] using (R,R)-i-Pr-DuPHOS and (S,S)-DPEN.

Other catalysts shown in the tables in Examples 4–8 were prepared similarly. Ligands used in the preparation of catalysts are selected from those identified above and from the following:

Typical General Procedure for Hydrogenation

Hydrogenations were carried out in 50 mL Parr hydrogenation vessels (or a Baskerville multi-welled hydrogenation vessel) equipped with an injection port with a rubber septum for the addition of the solvent using a syringe, a pressure gauge, a tightly fitting removable internal glass liner, and a magnetic stirring bar. Commercially available anhydrous i-PrOH was degassed prior to use, by sparging nitrogen for at least 30 minutes. A commercially available 1.0 M solution of t-BuOK in t-BuOH was used following degassing.

The catalyst (0.01 mmol) and imine substrate (1 mmol) were placed in the vessel, which was purged with nitrogen and then with hydrogen at least three times, by pressurising to 5 bar and releasing the pressure. i-PrOH (4 mL) was added and the reaction was purged three times with hydrogen. A solution of t-BuOK in t-BuOH (1.0 M, 1.0 mL, 1.0 mmol) was added and the reaction purged a further three times. Finally, the vessel was pressurised to 15 bar of hydrogen and stirred at 50–65° C. for 18–21 hours. When the pressure was released, a sample of the crude reaction was analysed (derivatised or underivatised) by chiral GC (DEX-CB column) for conversion and enantiomeric purity. Conversions were also determined using $^1$H NMR spectroscopy. Liquid imines were added to the catalyst in the purged vessel as a solution in i-PrOH. Variations from this procedure are described in the relevant tables and table footnotes, in the following Examples.

Hydrogenation substrates in the following Examples are either available commercially (Examples 5, 6 and 8) or may be prepared by the reaction of an amine and a ketone in toluene in the presence of 4A molecular sieves (Examples 4 and 7).

Example 4

Hydrogenation of N-(1-phenylethylidene)aniline

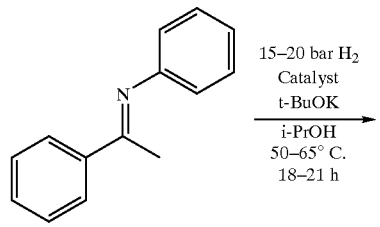

| Catalyst | Molar eq. t-BuOK | S/C | Conv. (%) | ee (%) |
|---|---|---|---|---|
| (S)-MeO-BIPHEP RuCl₂ (S,S)-ANDEN | 1 | 100 | 17 | 56 |
| (R)-MeO-BIPHEP RuCl₂ (R,R)-DPEN | 1 | 100 | 98 | 50 |
| (R)-BINAP RuCl₂ (R,R)-DPEN | 1 | 100 | 22 | 49 |
| (S)-Tol-BINAP RuCl₂ (S,S)-DPEN | 1 | 100 | 100 | 49 |
| (R,R)-Me-DuPHOS RuCl₂ (R,R)-DPEN | 1 | 100 | 94 | 85 |
| (R,R)-Me-DuPHOS RuCl₂ (R,R)-DPEN | 0.5 | 100 | 93 | 84 |
| (R,R)-Me-DuPHOS RuCl₂ (S,S)-DPEN | 1 | 100 | 36 | 16 |
| (S,S)-Et-DuPHOS RuCl₂ (S,S)-DPEN | 1 | 100 | 99 | 91 |
| (S,S)-Et-DuPHOS RuCl₂ (S,S)-DPEN | 0.5 | 100 | 99 | 89 |
| (S,S)-Et-DuPHOS RuCl₂ (R,R)-DPEN | 1 | 100 | 60 | 11 |
| (S,S)-i-Pr-DuPHOS RuCl₂ (R,R)-DPEN | 1 | 100 | 99 | 89 |
| (R,R)-Et-DuPHOS RuCl₂ (R,R)-DACH[a] | 0.1 | 1000 | 20 | 88 |
| (R,R)-Et-DuPHOS RuCl₂ (R,R)-DACH[b] | 0.05 | 1000 | 97 | 94 |

[a][substrate] = 0.5M; 20 hours reaction time
[b][substrate] = 4M; 69 hours reaction time

Example 5

Hydrogenation of 2,3,3-trimethylindolenine

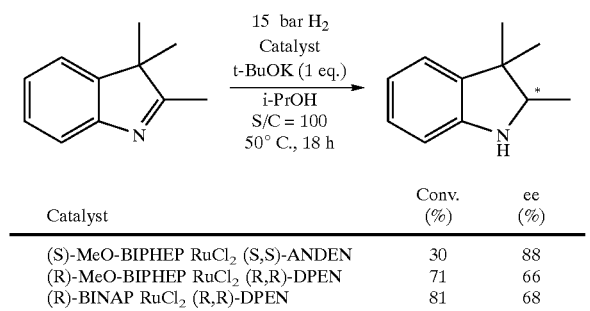

| Catalyst | Conv. (%) | ee (%) |
|---|---|---|
| (S)-MeO-BIPHEP RuCl₂ (S,S)-ANDEN | 30 | 88 |
| (R)-MeO-BIPHEP RuCl₂ (R,R)-DPEN | 71 | 66 |
| (R)-BINAP RuCl₂ (R,R)-DPEN | 81 | 68 |
| (S)-Tol-BINAP RuCl₂ (S,S)-DPEN | 86 | 67 |
| (S,S)-i-Pr-DuPHOS RuCl₂ (R,R)-DPEN | 25 | 53 |

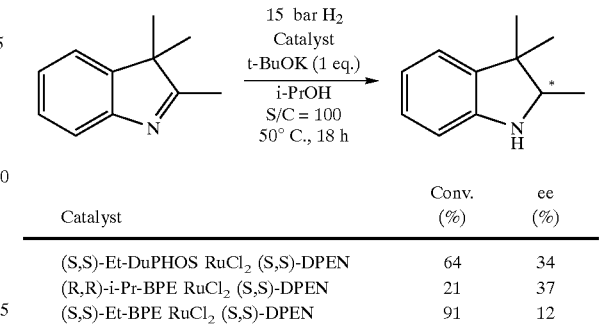

| Catalyst | Conv. (%) | ee (%) |
|---|---|---|
| (S,S)-Et-DuPHOS RuCl₂ (S,S)-DPEN | 64 | 34 |
| (R,R)-i-Pr-BPE RuCl₂ (S,S)-DPEN | 21 | 37 |
| (S,S)-Et-BPE RuCl₂ (S,S)-DPEN | 91 | 12 |

Example 6

Hydrogenation of 2-methylquinoxaline

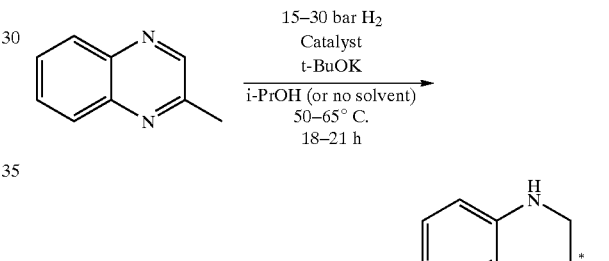

| Catalyst | Molar eq. t-BuOK | S/C | Conv. (%) | ee (%) |
|---|---|---|---|---|
| (S,S)-Et-BPE RuCl₂ (S,S)-DPEN | 1 | 100 | 98 | 39 |
| (R,R)-Me-BPE RuCl₂ (R,R)-DPEN | 1 | 100 | 86 | 29 |
| (S,S)-Et-DuPHOS RuCl₂ (S,S)-DPEN | 1 | 100 | 95 | 47 |
| (R,R)-Et-DuPHOS RuCl₂ (R,R)-DACH[a] | 0.05 | 1000 | 98 | 40 |
| (R)-NORPHOS RuCl₂ (R,R)-DPEN | 1 | 100 | 87 | 14 |
| (R)-3,5-Xylyl-Phanephos RuCl₂ (S,S)-DPEN | 1 | 100 | 89 | 45 |
| (S)-4-MeO-3,5-Xylyl-Phanephos RuCl₂ (R,R)-DPEN | 1 | 100 | 90 | 66 |
| (S)-MeO-BIPHEP RuCl₂ (S,S)-ANDEN | 1 | 100 | 61 | 16 |
| (R)-MeO-BIPHEP RuCl₂ (R,R)-DPEN | 1 | 100 | 92 | 41 |
| (S)-HexaPHEMP RuCl₂ (S,S)-DACH[a] | 0.05 | 1000 | 100 | 65 |
| (S)-HexaPHEMP RuCl₂ (S,S)-DACH | 1 | 100 | 94 | 81 |
| (S)-HexaPHEMP RuCl₂ (R,R)-DACH[a] | 0.05 | 1000 | 100 | 69 |
| (S)-HexaPHEMP RuCl₂ (S,S)-DPEN[a] | 0.05 | 1000 | 100 | 69 |
| (S)-HexaPHEMP RuCl₂ (R,R)-DPEN[a] | 0.05 | 1000 | 100 | 64 |
| (S)-BINAP RuCl₂ (S,S)-DACH[a] | 0.05 | 1000 | 100 | 61 |
| (R)-BINAP RuCl₂ (S,S)-DACH[a] | 0.05 | 1000 | 100 | 60 |
| (R)-BINAP RuCl₂ (R,R)-DPEN[a] | 1 | 100 | 87 | 55 |
| (R)-BINAP RuCl₂ (R,R)-DPEN[a] | 0.05 | 1000 | 99 | 66 |
| (R)-BINAP RuCl₂ (S,S)-DPEN[a] | 0.05 | 1000 | 100 | 66 |
| (R)-BINAP RuCl₂ (R)-DAIPEN[a] | 0.05 | 1000 | 94 | 62 |
| (S)-BINAP RuCl₂ (R)-DAIPEN[a] | 0.05 | 1000 | 96 | 37 |
| (S)-Tol-BINAP RuCl₂ (S,S)-DPEN | 1 | 100 | 92 | 57 |
| (S)-Tol-BINAP RuCl₂ (S,S)-DPEN[a] | 0.05 | 1000 | 100 | 68 |

[a]reaction run neat (no solvent)

Example 7

Hydrogenation of N-(1-phenylethylidene) benzylamine

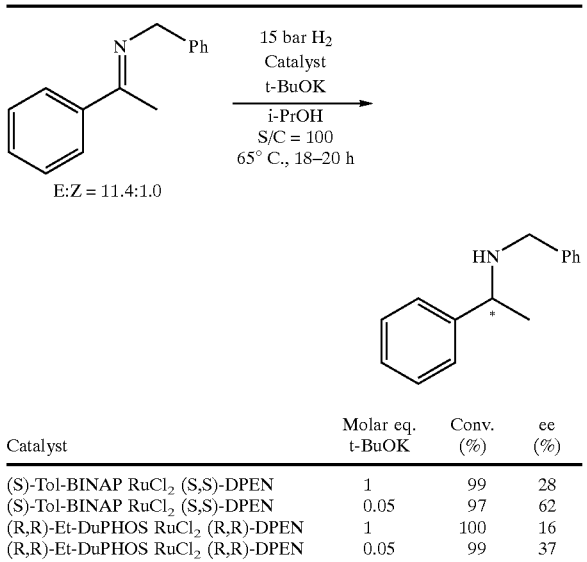

E:Z = 11.4:1.0

| Catalyst | Molar eq. t-BuOK | Conv. (%) | ee (%) |
|---|---|---|---|
| (S)-Tol-BINAP RuCl$_2$ (S,S)-DPEN | 1 | 99 | 28 |
| (S)-Tol-BINAP RuCl$_2$ (S,S)-DPEN | 0.05 | 97 | 62 |
| (R,R)-Et-DuPHOS RuCl$_2$ (R,R)-DPEN | 1 | 100 | 16 |
| (R,R)-Et-DuPHOS RuCl$_2$ (R,R)-DPEN | 0.05 | 99 | 37 |

Example 8

Hydrogenation of 1-methyl-6,7-dimethoxy-3,4-dihydroisoquinoline

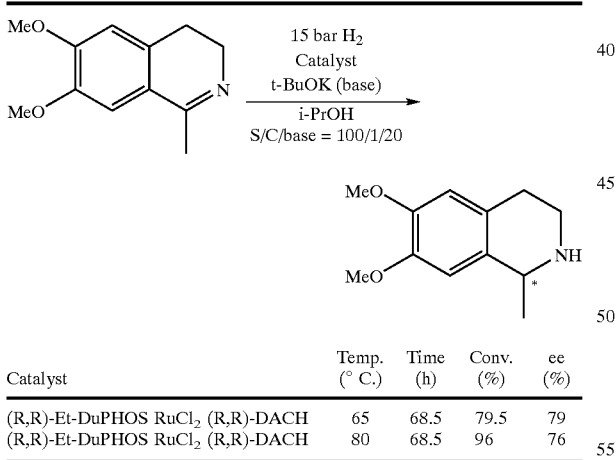

| Catalyst | Temp. (° C.) | Time (h) | Conv. (%) | ee (%) |
|---|---|---|---|---|
| (R,R)-Et-DuPHOS RuCl$_2$ (R,R)-DACH | 65 | 68.5 | 79.5 | 79 |
| (R,R)-Et-DuPHOS RuCl$_2$ (R,R)-DACH | 80 | 68.5 | 96 | 76 |

What is claimed is:

1. A process for the preparation of an enantiomerically enriched chiral amine of formula (10), or the opposite enantiomer thereof, from an imine of formula (11)

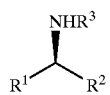

(10)

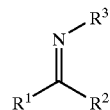

(11)

wherein (i) $R^1$ is aryl, $R^2$ is alkyl and $R^3$ is aryl or aryl-CH$_2$—, or (ii) $R^2$ is linked with $R^1$ and/or $R^3$ to form one or more rings and $R^3$ or $R^1$ (if not in a ring) is H or a non-interfering organic group, the number of C atoms in each of $R^1$, $R^2$ and $R^3$ being up to 30, which comprises asymmetric hydrogenation of the imine in the presence of a base and, as catalyst, a ruthenium complex of a chiral diphosphine and a chiral diamine.

2. A process according to claim 1, wherein $R^1$ and $R^3$ are each aryl and $R^2$ is alkyl, or $R^1$ and $R^2$ or $R^2$ and $R^3$ are linked to form a cycloalkyl ring having a fused aromatic ring.

3. The process according to claim 1, wherein $R^2$ and $R^3$ are linked to form a cyclic imine (11).

4. The process according to claim 1, wherein the ruthenium complex is an enantiomerically enriched compound of formula (DIP)RuX$_2$(DIA), or any of the possible diastereoisomers, in which DIP is a bis-tertiary phosphine in which the two phosphorus atoms are linked by a C$_{2-7}$ carbon chain such that they form a 5–10 membered ring with the Ru atom, X is halide or carboxylate, and DIA is a vicinal diamine with any aromatic, alkyl, or hydrogen substituent on the C$_2$-carbon chain linking the nitrogen atoms.

5. A process according to claim 4, wherein X is Cl, Br, I or F.

6. A process according to claim 5, wherein X is Cl.

7. The process according to claim 4, wherein DIP is an atropisomeric bis-tertiary phosphine in which the two phosphorus atoms are linked by a biaryl backbone.

8. A process according to claim 7, wherein DIP is selected from a binaphthyl ligand of formula (19), a biphenyl ligand of formula (12), and the opposite enantiomers thereof

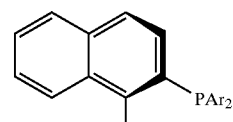

(19)

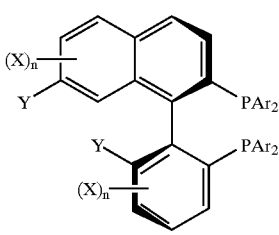

(12)

in which Ar is a phenyl group optionally substituted with up to two alkyl groups, Y is methyl or methoxy and (X)$_n$ represents one or more non-interfering substitutents.

9. The process according to claim 7, wherein the imine (11) is cyclic.

10. The process according to claim 7, wherein the imine (11) is acyclic and $R^3$ is aryl-CH$_2$-.

11. The process according to claim 4, wherein DIP is a ligand in which each P atom forms part of a phospholane ring.

12. A process according to claim 11, wherein DIP is a DuPHOS ligand of formula (13) or the opposite enantiomer thereof

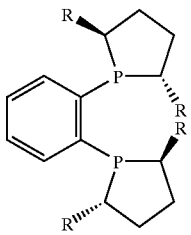

(13)

in which R is $C_{1-6}$ linear or branched alkyl.

13. A process according to claim 11, wherein DIP is methyl DuPHOS (R=Me) or ethyl DuPHOS (R=Et).

14. The process according to claim 11, wherein the imine (11) is acyclic and $R^3$ is aryl.

15. The process according to claim 11, wherein the imine (11) is a dihydroisoquinoline.

16. The process according to claim 4, wherein DIA is a diamine of general formula (14)

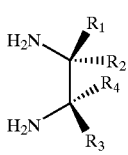

(14)

in which at least one of the amine-bearing centers is stereogenic, $R_1$, $R_2$, $R_3$ and $R_4$ are independently H, $C_{1-20}$, or $C_{6-20}$ aromatic group, or any pair of $R_1$, $R_2$, $R_3$, and $R_4$ is linked to form one or more rings.

17. A process according to claim 16, wherein DIA is selected from the compounds (15)–(19) and the opposite enantiomers thereof

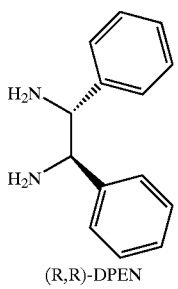

(15)

(R,R)-DPEN

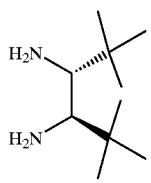

(16)

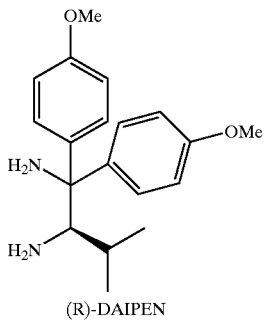

(17)

(R)-DAIPEN

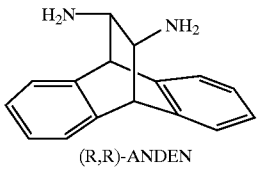

(18)

(R,R)-ANDEN

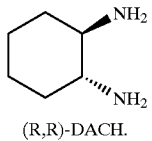

(19)

(R,R)-DACH.

18. A process according to claim 17, wherein DIA is (R,R)-DPEN and DIP is either (R,R)-methyl DuPHOS or (R,R)-ethyl DuPHOS, or the corresponding process in which a matched pair of (S,S)-stereoisomers is used.

19. The process according to claim 1, wherein the base is present in an amount sufficient to give substrate conversion of at least 80%.

20. A process according to claim 19, wherein the amount of the base is in the range of about 0.01–2 molar equivalents relative to the imine (11).

21. A process according to claim 20, wherein $R^1$ is aryl, $R^2$ is alkyl and $R^3$ is aryl-$CH_2$—and wherein the amount of additional base is about 0.05 equivalents or lower relative to the imine (11).

22. The process according to claim 19, wherein the base is an alkali metal alkoxide.

23. A process according to claim 22, wherein the base is potassium tert-butoxide or sodium isoproproxide.

24. The process according to claim 1, wherein the reaction is conducted in a solvent selected from the group consisting of isopropanol, ethanol, toluene, benzene, chlorobenzene and tetrahydrofuran.

25. A process according to claim 24, wherein the reaction solvent is isopropanol.

26. The process according to claim 1, wherein no reaction solvent is used.

27. The process according to claim 1, wherein enantiomeric enrichment of the amine (10) is at least 50% ee.

28. A process according to claim 27, wherein enantiomeric enrichment of the amine (10) is at least 80% ee.

* * * * *